| (12) | United States Patent | (10) Patent No.: | US 10,828,207 B2 |
|---|---|---|---|
| | Long et al. | (45) Date of Patent: | Nov. 10, 2020 |

(54) AUTOMATIC ABSORBENT ARTICLE CHANGE FEATURES

(71) Applicant: KIMBERLY-CLARK WORLDWIDE, INC., Neenah, WI (US)

(72) Inventors: Andrew Mark Long, Neenah, WI (US); Shawn J. Sullivan, Neenah, WI (US); Chris P. Olson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 713 days.

(21) Appl. No.: 15/526,913

(22) PCT Filed: Nov. 24, 2015

(86) PCT No.: PCT/US2015/062382
§ 371 (c)(1),
(2) Date: May 15, 2017

(87) PCT Pub. No.: WO2016/085960
PCT Pub. Date: Jun. 2, 2016

(65) Prior Publication Data
US 2017/0354548 A1 Dec. 14, 2017

Related U.S. Application Data

(60) Provisional application No. 62/084,715, filed on Nov. 26, 2014.

(51) Int. Cl.
*A61F 13/49* (2006.01)
*A61F 13/84* (2006.01)
*A61F 13/15* (2006.01)

(52) U.S. Cl.
CPC ........ *A61F 13/49* (2013.01); *A61F 13/15764* (2013.01); *A61F 13/84* (2013.01);
(Continued)

(58) Field of Classification Search
CPC .... A61F 13/49; A61F 13/15764; A61F 13/84; A61F 2013/8497; A61F 2013/8476;
(Continued)

(56) References Cited

U.S. PATENT DOCUMENTS 5,176,671 A 1/1993 Roessler et al.
5,423,789 A 6/1995 Kuen
(Continued)

FOREIGN PATENT DOCUMENTS

CA 2751014 A1 * 2/2013 ............. A61G 12/00
CN 101478939 A 7/2009
(Continued)

*Primary Examiner* — Nicholas J. Weiss
*Assistant Examiner* — Gabriella E Burnette
(74) *Attorney, Agent, or Firm* — Kimberly-Clark Worldwide, Inc.

(57) ABSTRACT

A system for removing and donning a disposable absorbent article by using a separate robotic device includes an absorbent assembly having an inner layer that partly defines a body-facing surface, an outer layer that defines a garment-facing surface, and an absorbent body disposed between the inner and outer layers. The absorbent assembly also includes a pair of ears extending transversely outward from the opposite sides of the absorbent assembly in the back waist region, each of the ears including a body-facing surface with a primary first fastening-component that is selectively engageable with a primary second fastening-component in the front waist region of the absorbent assembly in a wear configuration of the article, and a garment-facing surface opposite the body-facing surface. The absorbent article also includes a manipulation-enablement feature configured to assist the post-retail manipulation of the absorbent article by the robotic device.

17 Claims, 3 Drawing Sheets

(52) U.S. Cl.
CPC ............... *A61F 2013/49047* (2013.01); *A61F 2013/8476* (2013.01); *A61F 2013/8497* (2013.01)

(58) Field of Classification Search
CPC .... A61F 2013/49047; A61F 2013/8482; B25J 19/021; B25J 11/009
See application file for complete search history.

(56) References Cited

U.S. PATENT DOCUMENTS

| | | | |
|---|---|---|---|
| 5,704,933 A | 1/1998 | Fell et al. | |
| 5,751,214 A | 5/1998 | Cowley et al. | |
| 5,766,389 A | 6/1998 | Brandon | |
| 6,603,403 B2 | 8/2003 | Jeutter et al. | |
| 6,774,800 B2 | 8/2004 | Friedman et al. | |
| 6,870,479 B2 | 3/2005 | Gabriel | |
| 7,306,764 B2 * | 12/2007 | Mody | G01N 31/222 422/401 |
| 7,321,315 B2 | 1/2008 | Brumm et al. | |
| 7,344,525 B2 | 3/2008 | Linker, III et al. | |
| 7,699,222 B2 | 4/2010 | Uchitani | |
| 8,057,454 B2 | 11/2011 | Long et al. | |
| 8,137,290 B2 | 3/2012 | Zhang et al. | |
| 8,237,572 B2 | 8/2012 | Clement et al. | |
| 8,376,232 B2 | 2/2013 | Eckstein et al. | |
| 8,421,636 B2 | 4/2013 | Collette et al. | |
| 8,492,451 B2 | 7/2013 | Luo | |
| 8,579,875 B2 | 11/2013 | Shimizu et al. | |
| 8,632,463 B2 | 1/2014 | Drinan et al. | |
| 8,728,052 B2 * | 5/2014 | Wang | A61F 13/511 604/399 |
| 9,220,640 B2 * | 12/2015 | Ales | A61F 13/84 |
| 2004/0097896 A1 * | 5/2004 | Raufman | A61F 13/5633 604/385.01 |
| 2004/0245069 A1 | 12/2004 | Hook | |
| 2008/0021423 A1 | 1/2008 | Klofta et al. | |
| 2008/0312632 A1 | 12/2008 | Fernfors | |
| 2010/0147722 A1 * | 6/2010 | Datta | A61F 13/84 206/440 |
| 2011/0095884 A1 | 4/2011 | Xu et al. | |
| 2012/0061155 A1 * | 3/2012 | Berger | B25J 5/007 180/21 |
| 2012/0173249 A1 * | 7/2012 | Popp | A61F 13/51496 705/1.1 |
| 2012/0268278 A1 | 10/2012 | Lewis et al. | |
| 2013/0032634 A1 | 2/2013 | McKirdy | |
| 2013/0052432 A1 | 2/2013 | Koebel et al. | |
| 2013/0138450 A1 | 5/2013 | Vigneux | |
| 2014/0022058 A1 | 1/2014 | Striemer et al. | |
| 2014/0063085 A1 | 3/2014 | Warner et al. | |
| 2014/0296816 A1 * | 10/2014 | Paveletzke | A61F 13/4906 604/385.01 |
| 2015/0273698 A1 * | 10/2015 | Bender | B25J 11/009 701/23 |
| 2016/0058631 A1 * | 3/2016 | Ormsby | A61F 13/5644 604/391 |

FOREIGN PATENT DOCUMENTS

| | | |
|---|---|---|
| CN | 101668500 A | 3/2010 |
| CN | 103753578 A | 4/2014 |
| JP | 2008-264232 A | 11/2008 |
| WO | WO 1995/005140 A1 | 2/1995 |
| WO | WO 1997/038658 A1 | 10/1997 |
| WO | WO 2013/013197 A1 | 1/2013 |
| WO | WO 2013/095222 A1 | 6/2013 |
| WO | WO 2013/095230 A1 | 6/2013 |

* cited by examiner

AUTOMATIC ABSORBENT ARTICLE CHANGE FEATURES

BACKGROUND

The present disclosure relates generally to absorbent articles intended for personal wear, and more particularly to disposable absorbent articles having a fastening system for selectively fastening and refastening the article about the wearer.

Many absorbent articles intended for personal wear, such as diapers, training pants, feminine hygiene products, adult incontinence products, bandages, medical garments and the like are designed to be sufficiently absorbent to absorb moisture from liquid body exudates including urine, menses, blood, etc., away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs, and left in place to absorb insults as well as to contain fecal waste.

The home is becoming automated and connected as the "internet of things" grows. Many companies have also been investing in home automation such as robotics and drones to do work and deliver goods and services. Products need to be designed to work with these systems. Design elements and materials enable products to fit this new paradigm. Absorbent articles do not have design elements that enable an automated system to identify and engage with the product.

There is a need, therefore, for diaper design elements that enable a robotic system to identify, grasp, open, apply, and fasten an absorbent product. While many of the features are designed for a caregiver, such as finger tabs, modifications of these features enable robotic-specific application and disposal. Robots sense things differently, such as the stress/strain curve for fastener application, and robots are actually better at providing, for example a secure and more consistent fastening. Such a system can be enabled by the technical data available to the system and identified on the product.

SUMMARY

The present disclosure describes a system for removing and donning a disposable absorbent article by using a separate robotic device, the system including an absorbent assembly including longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly. The absorbent assembly also includes a pair of ears extending transversely outward from the opposite sides of the absorbent assembly in the back waist region, where each of the ears includes a body-facing surface with a primary first fastening-component that is selectively engageable with a primary second fastening-component in the front waist region of the absorbent assembly in a wear configuration of the article, and a garment-facing surface opposite the body-facing surface. The absorbent article also includes a manipulation-enablement feature configured to assist the post-retail manipulation of the absorbent article by the robotic device.

The present disclosure also describes a system for removing and donning a disposable absorbent article by using a separate robotic device, the system including an absorbent assembly including longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly. The absorbent assembly also includes a pair of ears extending transversely outward from the opposite sides of the absorbent assembly in the back waist region, each of the ears including a body-facing surface with a primary first fastening-component that is selectively engageable with a primary second fastening-component in the front waist region of the absorbent assembly in a wear configuration of the article, and a garment-facing surface opposite the body-facing surface. The absorbent article also includes a manipulation-enablement feature configured to assist the post-retail manipulation of the absorbent article by the robotic device, wherein the manipulation-enablement feature includes at least one of an engagement member disposed on the garment-facing surface of each of the pair of ears, each engagement member configured to selectively engage the robotic device, alignment fastener indicia disposed on one of the body-facing and garment-facing surfaces of the absorbent assembly, and manipulation indicia disposed on one of the body-facing and garment-facing surfaces of the absorbent assembly.

The present disclosure also describes a method for removing and donning a disposable absorbent article using a separate robotic device, the method including providing a system including an absorbent assembly including longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly. The absorbent assembly also includes a pair of ears extending transversely outward from the opposite sides of the absorbent assembly in the back waist region, each of the ears including a body-facing surface with a primary first fastening-component that is selectively engageable with a primary second fastening-component in the front waist region of the absorbent assembly in a wear configuration of the article, and a garment-facing surface opposite the body-facing surface. The absorbent article also includes a manipulation-enablement feature configured to assist the post-retail manipulation of the absorbent article by the robotic device. The method also includes providing a changing station including an application section, the application section including an application surface wherein the absorbent assembly can be selectively disposed in an unfastened and unused state; and a removal section including a removal surface configured for the removal of the absorbent assembly from the wearer. The method also includes engaging the separate robotic device for the placement of an unused, unfastened absorbent assembly onto the application surface such that the garment-facing surface is directly or indirectly adjacent to the application surface.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
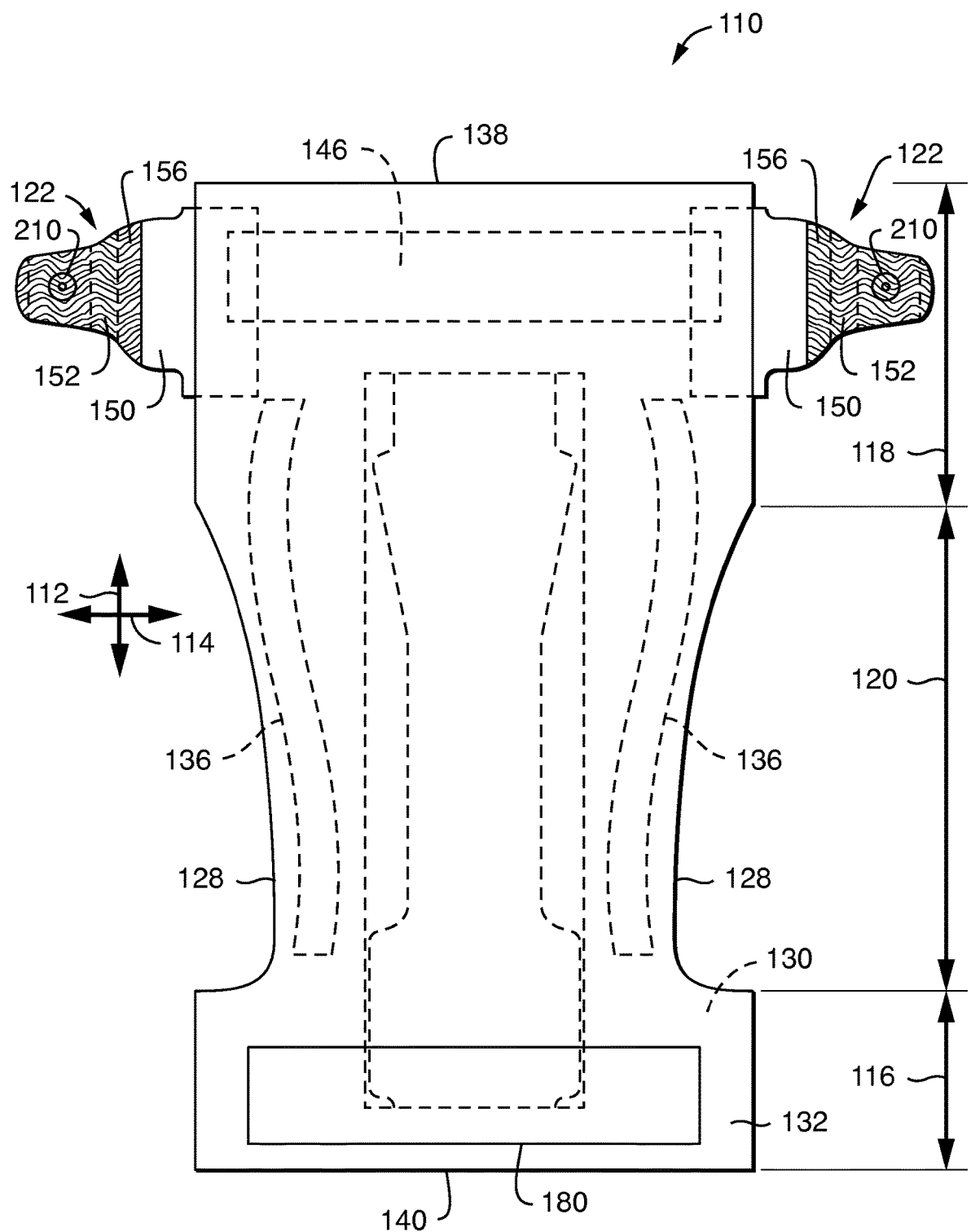
FIG. 1 is a top plan view of a diaper according to one aspect of the present disclosure in an unfolded and laid flat condition to show an outer surface of the diaper that faces away from the wearer when the diaper is worn.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

According to some aspects of the disclosure, an absorbent article is provided that overcomes at least some of the deficiencies of the conventional diapers described above.

Figure 2:
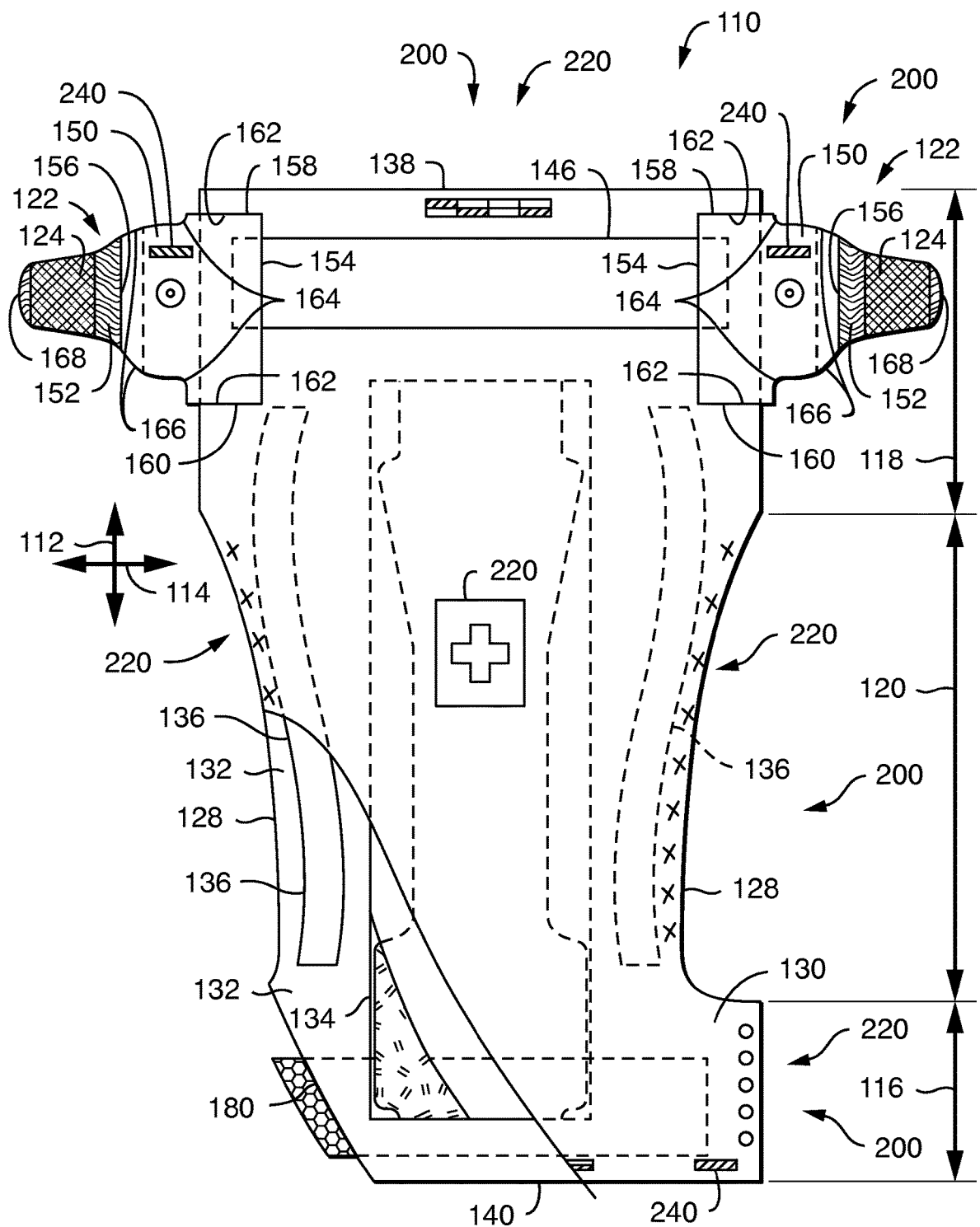
FIG. 2 is a partially cut away bottom plan view of the diaper of FIG. 1 in an unfolded and laid flat condition to show an inner surface of the diaper that faces towards the wearer when the diaper is worn.

These features will become more apparent with reference to the accompanying drawings. FIGS. 1 and 2 illustrate one suitable aspect of a diaper (broadly, "an absorbent article"), indicated generally at 110, in an unfolded and laid flat condition to show an outer surface of the diaper 110 that faces away from the wearer when the diaper 110 is worn (FIG. 1) and an inner surface of the diaper 110 that faces the wearer when the diaper 110 is worn (FIG. 2). Portions of the diaper 110 illustrated in FIG. 2 are cut away to illustrate underlying structures. The diaper 110 has a longitudinal direction 112 and a lateral direction 114. While the present description will be made in the context of a diaper 110, it should be understood that the present disclosure is also applicable to other personal care absorbent articles, such as adult incontinence garments, children's training pants, swim pants, and the like.

In one suitable aspect, the diaper 110 is a disposable absorbent article. As used herein, the term "disposable absorbent article" refers to articles that absorb and contain body exudates and that are intended to be discarded after a limited period of use. The articles are not intended to be laundered or otherwise restored for reuse. The articles can be placed against or in proximity to the body of a wearer to absorb and contain various exudates discharged from the body. It is understood that in other suitable aspects, the diaper 110 can be reusable. That is, the diaper 110 can be intended for multiple uses without departing from some aspects of this disclosure.

In the longitudinal direction 112, the diaper 110 defines a front portion 116, a back portion 118, and a crotch portion 120 extending between and connecting the front portion and the back portion. The diaper 110 includes a bodyside liner 130, an outer cover 132, and an absorbent core 134 located between the bodyside liner 130 and the outer cover 132. The bodyside liner 130, outer cover 132 and absorbent core 134 collectively define an absorbent assembly. The absorbent assembly can be any suitable shape including, for example, generally I-shaped as illustrated in FIGS. 1 and 2. As used herein, reference to the front portion 116 refers to that part of the diaper 110 that is generally located on the front of a wearer when in use. Reference to the back portion 118 refers to the portion of the diaper 110 generally located at the back of the wearer when in use, and reference to the crotch portion 120 refers to that portion that is generally located between the legs of the wearer when in use.

In the illustrated aspect, the back portion 118 includes a straight back waist edge 138 and the front portion 116 includes a straight front waist edge 140. As used herein, "straight edge" refers to edges that are substantially free from curves, bends, angles, notches, or irregularities. It is understood, however, that the back waist 138 and the front waist 140 can be cut in any suitable shape as are known in the art (e.g., arcuate). As seen in FIGS. 1 and 2, the diaper 110 has opposite longitudinal side edges 128 that extend between the back waist edge 138 and the front waist edge 140. In the illustrated aspect, each of the side edges 128 includes an arcuate portion for defining a portion of a leg opening during wear of the diaper 110.

The bodyside liner 130 of the diaper 110, as illustrated in FIG. 2, defines a body facing surface that is intended to be worn adjacent and in directed contact with the body of the wearer. The bodyside liner 130 can be suitably compliant, soft feeling and nonirritating to the wearer's skin. The bodyside liner 130 can be less hydrophilic than the absorbent core 134 and sufficiently porous to be liquid permeable. The bodyside liner 130 can be manufactured from a wide selection of suitable web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 130 is suitably adapted to isolate the wearer's skin from liquids and moisture held by the absorbent core 134.

The outer cover 132 of the diaper 110, which is illustrated in FIG. 1, defines a garment-facing surface that is intended to be worn adjacent the clothing of the wearer. In one suitable aspect, the outer cover 132 is a polyethylene film. In another suitable aspect, the outer cover 132 includes a woven or non-woven fibrous web layer that has been totally or partially constructed or treated to impart a desired level of liquid impermeability to selected regions of the outer cover 132 that are adjacent or proximate the absorbent core 134. For example, a cloth-like outer cover 132 can be composed of polypropylene spunbond fabric that is laminated and thermally bonded to a stretch-thinned polyethylene film. The outer cover 132 can include a micro-porous, "breathable" material that permits vapors to escape from diaper 110 while still preventing liquid exudates from passing through. For example, the outer cover 132 can be composed of a microporous polymer film or a nonwoven fabric that has been coated or otherwise treated to impart a desired level of liquid impermeability. The outer cover 132 can also be embossed or otherwise provided with a matte finish to exhibit a more aesthetically pleasing appearance.

The bodyside liner 130 and the outer cover 132 are generally joined in facing relationship with the absorbent core 134 located therebetween. The bodyside liner 130 and the outer cover 132 can be joined to each other around the outer periphery of the diaper 110 by any means known to those skilled in the art such as adhesive bonds, ultrasonic bonds, thermal bonds, and the like, and combinations thereof. As used herein, the term "join", and derivatives thereof, encompass configurations wherein an element is directly secured to the other element by affixing the element directly to the other element, and configurations wherein the element is indirectly secured to the other element by affixing the element to intermediate member(s) that in turn are affixed to the other element.

As mentioned above, the absorbent core 134 is positioned between the bodyside liner 130 and the outer cover 132. The absorbent core 134 is generally conformable and capable of absorbing and retaining liquid body exudates. The absorbent core 134 can include superabsorbent material, staple fibers, binder fibers, and the like, and combinations thereof as is known in the art. The absorbent core 134 can have any of a number of shapes and sizes. For example, the composite absorbent core 134 can be rectangular, I-shaped, or T-shaped. The size and absorbent capacity of the absorbent core 134 should be compatible with the size of the intended wearer and the fluid loading imparted by the intended use of the diaper.

In one suitable aspect, the diaper 110 can include a surge portion (not shown) disposed between the absorbent core 134 and the bodyside liner 130. The surge portion serves to quickly collect and temporarily hold liquids discharged by the wearer and then release the liquids to the absorbent core 134. Various woven and nonwoven materials can be used to construct the surge portion. For example, the surge portion can be a layer of a spunbonded or meltblown web of polyolefin fibers. The surge portion can also be a bonded carded web of natural and synthetic fibers. The surge portion can be a substantially hydrophobic material and, optionally, can be treated with a surfactant or otherwise to impart a desired level of wettability and hydrophilicity.

The diaper 110 includes a pair of elasticized, longitudinally-extending leg cuffs 136. The leg cuffs 136 are adapted to fit about the legs of a wearer in use and serve as a mechanical barrier to the lateral flow of body exudates. In one suitable aspect, the leg cuffs 136 can be formed by portions of the outer cover 132, and/or bodyside liner 130, which extend beyond the longitudinal sides of the absorbent core 134. In another suitable aspect, the leg cuffs 136 can be formed from separate materials (e.g., stands of leg elastics) joined to the outer cover 132 and/or the bodyside liner 130.

The diaper 110 can further include front waist elastic (not shown) and/or back waist elastic 146. In the illustrated aspect, for example, the diaper 110 has back waist elastic 146 but not front waist elastic. The back waist elastic 146 is arranged to draw and hold the diaper 110 against the wearer, particularly against the waist of the wearer, as will be more fully discussed.

Materials suitable for use in forming leg cuffs 136 and/or waist elastics 146 are known to those skilled in the art. Examples of such materials are strands or ribbons of a polymeric, elastomeric material that are adhered to the diaper 110 in a stretched position, or that are attached to the diaper while the diaper is pleated, such that elastic constrictive forces are imparted to the diaper. The leg cuffs 136 and/or waist elastics 146 can have any configuration that provides the desired performance. The leg cuffs 136 can be generally straight or optionally curved (as illustrated in FIGS. 1 and 2) to more closely fit the contours of the legs of the wearer. As used herein, "elastic," "elastomeric," and the like refer to the ability of a material or composite to be elongated by at least about 50 percent and upon relaxation to return to within at least 50 percent of its original length.

The leg cuffs 136 and/or waist elastics 146 can be attached to the diaper 110 in any way known to those skilled in the art. For example, the leg cuffs 136 and/or waist elastics 146 can be joined to the diaper 110 by ultrasonic bonding, thermal bonding, adhesive bonding, and the like, and combinations thereof.

The diaper 110 can also include a pair of containment flaps (not shown) that extend longitudinally along the diaper and are adapted to provide a barrier to the lateral flow of body exudates. The containment flaps can be connected to the bodyside liner 130 or other components as is well known in the art. Suitable configurations of the containment flaps are described, for example, in U.S. Pat. No. 5,599,338 issued Feb. 4, 1997, to K. Enloe, the entirety of which is incorporated herein by reference.

As seen in FIGS. 1 and 2, the back portion 118 of the diaper includes a pair of back ears, indicated generally at 122. In one suitable aspect, the back ears 122 can be formed from extensions of the bodyside liner 130, the outer cover 132, or combinations of both the bodyside liner and the outer cover 132. In another suitable aspect, and as illustrated in FIGS. 1 and 2, the back ears 122 can be formed as separate components and attached to the bodyside liner 130, the outer cover 132, or both the bodyside liner and the outer cover 132 as is known in the art. In the illustrated aspect, the back ears 122 are attached to the body-facing surface of the bodyside liner 130 such that the attached portion of the ears 122 are disposed between the wearer's body and bodyside liner 130 when the diaper 110 is worn.

In one suitable aspect, each of the back ears 122 includes an elastomeric portion 150, a non-elastomeric portion 152, and a primary first fastening component 124 mounted to the non-elastomeric portion 152 (FIG. 2). Each of the elastomeric portions 150 has a proximal edge 154, an opposed distal edge 156, an upper edge 158, and a lower edge 160. As seen in FIG. 2, the proximal edge 154 of each of the elastomeric portions 150 is spaced inward from the respective side edge 128 of the diaper 110 such that a portion of the elastomeric portion 150 overlaps the bodyside liner 130. The part of each of the elastomeric portions 150 overlapping the bodyside liner 130 is bonded (e.g., adhesive bonding, thermal bonding, both thermal and adhesive bonding) to at least the bodyside liner 130. In another suitable aspect, the elastic component 150 can be eliminated and the entire back ear 122 can be constructed from the non-elastic component 152.

In the aspect illustrated in FIGS. 1 and 2, the proximal edge 154 and the distal edge 156 of each of the elastomeric portions 150 are generally parallel with respect to each other, and both are straight (i.e., linear). In one suitable aspect, the proximal edge 154 has a length from about 2 inches (5.1 centimeters) to about 7 inches (17.8 centimeters), preferably from about 3 inches (7.6 centimeters) to about 6 inches (15.2 centimeters), and more preferably from about 3.5 inches (8.9 centimeters) to about 5.5 inches (14.0 centimeters). The distal edge 156 has a length from about 0.25 inch (0.635 centimeter) to about 6 inches (15.24 centimeters), and preferably from about 1 inch (2.54 centimeters) to about 3 inches (7.6 centimeters). Further, the ratio of the length of the distal edge 156 to the proximal edge 154 is suitably from about 1:28 to about 3:4, and, and preferably from about 1:10 to about 2:3, and more preferably from about 1:4 to about 1:2.

Both the upper and lower edges 158, 160 have first segments 162 that are generally parallel to each other and generally perpendicular to the respective proximal edges 154. Each of the first segments 162 generally correspond to the part of each of the elastomeric portions 150 that overlap the bodyside liner 130. In the illustrated aspect, the first segments 162 of the upper edges 158 of the elastomeric portion 150 are spaced from the back waist edge 138. It is understood, however, that the first segments 162 can be aligned with the back waist edge 138 of the diaper 110.

Second segments 164 of each of the upper and lower edges 158, 160 are generally coaxial and extend towards each other generally perpendicular to the first segments 162. In the illustrated aspect, the second segment 164 of the lower edge 160 has a length greater than the length of the second segment of the upper edge 158. It is understood, however, that the second segments 164 of the upper and lower edges 158, 160 can have any suitable length.

Each of the illustrated elastomeric portions 150 includes an arcuate third segment 166 interconnecting the second segments 164 to the respective distal edge 156. In the illustrated aspect, the third segments 166 are generally mirror images of each other. It is understood, however, that the third segments 166 can have any suitable shape and that the third segments of the upper edges 158 can have a shape that is different that the shape of the third segments of the lower edges 160.

The elastomeric portions 150 of the back ears 122 can be formed from any type of elastomeric material capable of performing as described herein. In one suitable aspect, the elastomeric material will be stretchable in at least one direction (e.g., in the lateral direction 114 of the diaper 110 as viewed in FIGS. 1 and 2) and alternatively, the elastomeric material will be stretchable in two directions (e.g., in both the longitudinal direction 112 and the lateral direction of the diaper as viewed in FIGS. 1 and 2). Suitably when the elastomeric material is stretchable in a single direction, the stretch direction of the elastomeric material will be oriented so as to provide elastomeric forces that tend to pull the front and rear portions of the article towards one another such that the article is maintained about the waist of a wearer.

In one suitable aspect, the elastomeric material from which the elastomeric portions 150 of the back ears 122 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material can be an inherently elastomeric material, that is, one that is formed in an elastomeric state, or can be rendered elastomeric through processing subsequent formation. For example, the elastomeric material can be heat or pressure activated. The elastomeric portions 150 of the back ears 122 can be formed from a stretch-bonded-laminate (SBL) material, a neck-bonded-laminate (NBL) material, an elastomeric film, an elastomeric foam material, or the like.

Each of the non-elastomeric portions 152 of the back ears 122 is attached to a respective one of the elastomeric portions 150, and the primary first fastening components 124 (such as a hook material) are in turn disposed on the non-elastomeric portions 152. As illustrated in FIGS. 1 and 2, the non-elastomeric portions 152 of the back ears 122 extend in part transversely outward of the respective elastomeric portion 150 and the primary first fastening component 124 of each of the non-elastomeric portions 152 are configured for engaging a loop component disposed in the front waist region 116 of the diaper 110 in the wear configuration, as will be discussed more fully.

As seen best in FIG. 2, each of the illustrated non-elastomeric portions 152 further include a grip region 168 transversely outward of the primary first fastening component 124 for use in manually gripping and manipulating the non-elastomeric portion and more broadly the respective back ear 122 relative to the diaper 110. The grip region 168 is non-attachable to the diaper 110. The term "non-attachable" as used in this instance means that the grip region 168 is not releasably or otherwise removably attachable to the diaper 110. In one aspect, the grip region 168 extends transversely outward from the respective primary first fastening component 124 a distance of at least about 1 mm, such as in the range of about 1 mm to about 10 mm to provide sufficient unattached material for readily gripping and pulling on the non-elastomeric portion 152.

Figure 3:
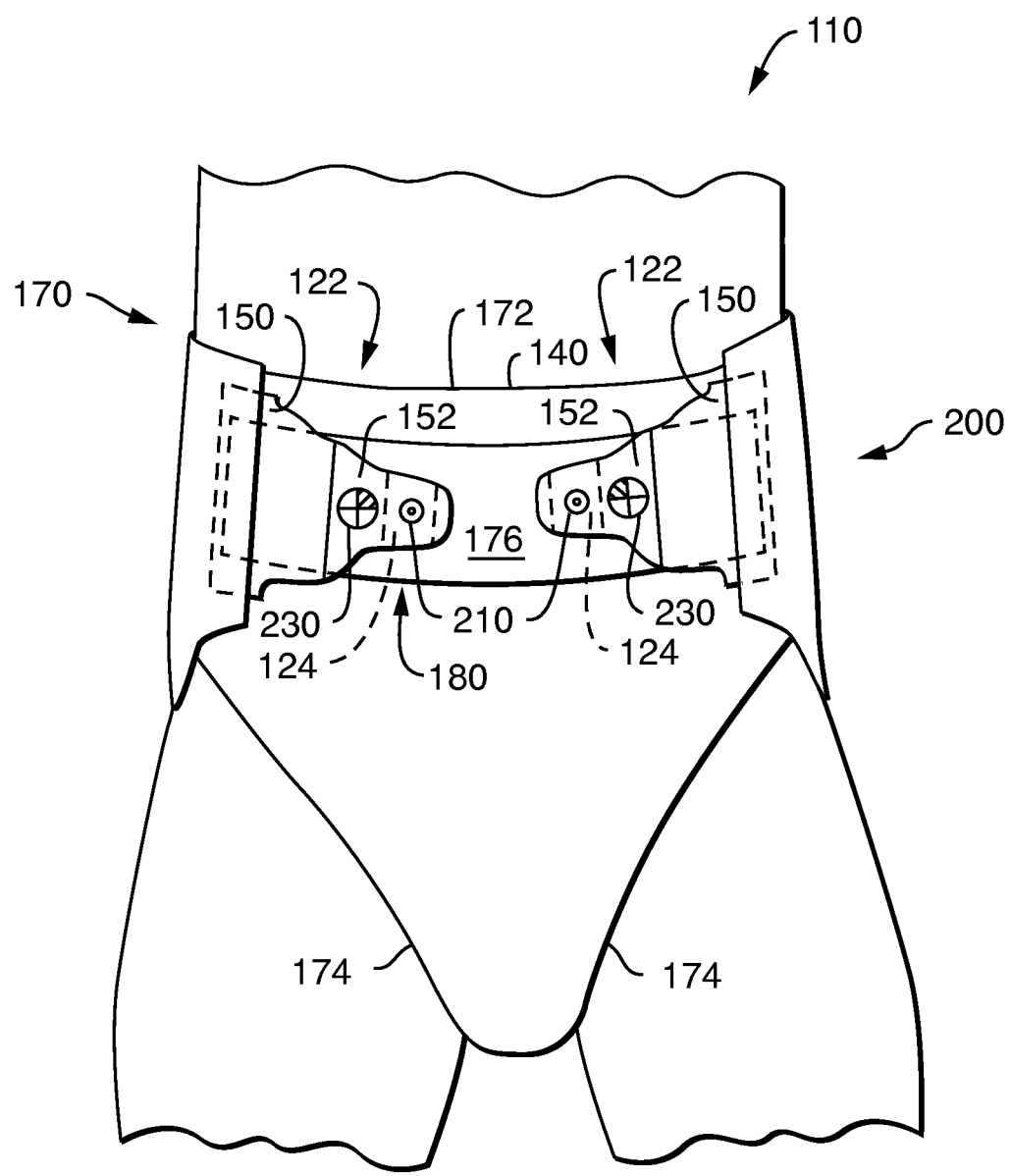
FIG. 3 is a front view of the diaper of FIG. 1 in a wear configuration with the fastening system fastened.

The diaper 110 can be selectively moved from the unfastened configuration, as illustrated in FIGS. 1 and 2, to a fastened or wear configuration as illustrated in FIG. 3, by attaching the back waist region 118 (and more specifically the back ears 122) to the front waist region 116 using an article fastening system 170 to define a three-dimensional wear configuration of the diaper having a waist opening 172 and a pair of leg openings 174. Although the diaper 110 illustrated in FIG. 3 shows the back waist region 118 (and more specifically the back ears 122) overlapping the front waist region 116 upon connection thereto, which is convenient, the diaper 110 can also be configured so that the front waist region 116 overlaps the back waist region 118 when connected.

According to some aspects, the article fastening system 170 includes a primary fastening system. The primary fastening system includes the primary first fastening components 124 disposed on the non-elastomeric portions 152 of the back ears 122 and at least one corresponding primary second fastening component 176 that is adapted for refastenable engagement to the primary first fastening components 124. In one suitable aspect, an outer surface of each of the primary fastening components 124, 176 includes a plurality of engaging elements. More specifically, the engaging elements of the primary first fastening components 124 are adapted to repeatedly engage and disengage corresponding engaging elements of the primary second fastening components 176 to releasably secure the diaper 110 in its wear configuration.

The primary fastening components 124, 176 can include any refastenable fasteners suitable for absorbent articles, such as adhesive fasteners, cohesive fasteners, mechanical fasteners, or the like. In one suitable aspect, the primary fastening components 124, 176 include mechanical fastening components, such as hook and loop fasteners. For example, suitable hook and loop components can be provided by interlocking geometric shaped materials. As used herein, "hook" broadly refers to any suitable mechanical fastener adapted to engage loop components including, e.g., hooks, bulbs, mushrooms, arrowheads, balls on stems, stems, structures having stems that engage foam such as open cell foam or the like, etc. Other suitable mechanical fastening components include male and/or female mating components, buckles, snaps, or the like. In the illustrated aspect, the primary first fastening components 124 include hook fasteners and the primary second fastening components 176 include a complementary loop fastener disposed on the outer surface of the outer cover 132. Alternatively, the primary first fastening components 124 can include loop fasteners and the primary second fastening components 176 can include complementary hook fasteners.

The shape, density, and polymer composition of the hooks and loops can be selected to obtain the desired level of engagement between the primary fastening components 124, 176. A more aggressive hook material can include a material with a greater average hook height and/or a greater percentage of directionally-aligned hooks.

In some aspects, the outer facing surface of the outer cover 132 of the diaper 110 is suitably constructed to define the primary second fastening component 176, which is a loop fastener. That is, the outer cover 132 itself can be formed of a material that defines the primary second fastening component 176 (e.g., vertical filament laminate (VFL) or other suitable material).

In another suitable aspect, and as illustrated in FIG. 3, the primary second fastening component 176 can be formed as a separate component and attached to the outer surface of the diaper's outer cover 132. More specifically, a strip, indicated generally at 180, including loop fastening material is attached to the front waist region 116 of the diaper 110.

The absorbent article or diaper 110 is provided with features that assist a robotic device in seeing, aligning with, and grasping the absorbent article 110. With such assistance, the robotic device can be used for removing and donning a disposable absorbent article 110. Included is a series of absorbent article features that, when combined as a system, enable a robotic absorbent article application. These features include information integrated into the absorbent article 110 or adjacent elements such as packaging to enable the robotic system to identify critical design elements and interact with them. Included in such features is a manipulation-enablement feature 200 configured to assist the post-retail manipulation of the absorbent article 110 by the robotic device. Post-retail manipulation refers to manipulation of the absorbent article 110 in a consumer or other caregiver environment after the absorbent article 110 has been purchased or otherwise acquired by a consumer.

There are two primary product modifications that enable this system. The first is modifications to the product to enable a robotic system to grasp or manipulate the absorbent article 110. This will enable the system to open the article package, grasp an absorbent article 110, remove the absorbent article 110 from the bag, and transport it to the changing surface. The system can then open the absorbent article 110 for application so the wearer can be placed on it, and then grasp and fasten the fasteners on the absorbent article 110. For removal of the article, the fasteners again need to be grasped, unfastened, and the absorbent article 110 unfolded so the wearer can be removed from proximity of the absorbent article 110. The absorbent article 110 then needs to be wrapped up for disposal. Grip regions on the folded edge of the absorbent article 110 will enable a system to grab and remove the absorbent articles 110 from the bag.

In one aspect of the present disclosure, the manipulation-enablement feature 200 includes an engagement member 210 disposed on the garment-facing or body-facing surfaces of each of the pair of ears 122, where each engagement member 210 is configured to selectively engage the robotic device. To be able to close the absorbent article 110 around a wearer, the robotic device must be able to grasp or otherwise engage the ears 122 to bring them around the wearer and to engage the fastener components on the ears 122 with the fastener components on the front of the absorbent article 110. The engagement member 210 can be hook material, loop material, a snap, an adhesive, a cohesive, or any other suitable means to assist the robotic device in engaging the absorbent article 110. In a specific, non-limiting example, loop material can be disposed on the ears 122 of the absorbent article 110 either in addition to the structures already present on the absorbent article 110, or as an inherent feature of one of the structures of the absorbent article 110. In this example, the robotic device is then provided with hook material to allow the hook material of the robotic device to engage with the loop material of the absorbent article 110, thereby allowing the robotic device to manipulate the absorbent article 110. Other aspects include tabs that extend and are grasped by automated fingers or snaps or mechanical systems that can be clipped or snapped into.

A second set of modifications enables the system's vision system using product edges and other structures that are identifiable. For example, a robotic system can be designed to have an ultraviolet (UV) light source and sensors that detect fluorescent construction adhesive used in the absorbent article 110. The fluorescence of the adhesive would reliably distinguish the absorbent article 110 from its surroundings and highlight its outline, enabling a robotic system to grasp the absorbent article 110 at the desired locations for safely changing the absorbent article 110. Hot melt adhesives used in the manufacture of diapers and pants currently contain UV dyes that fluoresce under UV (black light), so this solution is economical. The fluorescence is only seen under UV light so the aesthetics of the absorbent article 110 are not affected under normal light.

Indicia that have designs that are visually distinct will enable the system to identify the product edges (perimeter), the folded edge of the absorbent article 110, the fasteners, and the areas that the fasteners should attach to. QR code stickers or other identification tags placed or printed on the outer cover 132 or the like are read by optical sensors in the robotic system. The robotic system is then linked to information about the absorbent article 110, including the location of design elements such as fastener configuration and product size and functional information including absorbency, gender, size, etc. of the absorbent article 110. Such information also enables one robotic system to care for any number of wearers using any number of different product types, sizes, etc. on each child.

In another aspect of the present disclosure, the manipulation-enablement feature 200 includes alignment indicia 220 and/or fastener indicia 230 disposed on one or both of the body-facing and garment-facing surfaces of the absorbent article 110. Alignment indicia 220 are visual indicia that an automated system can use to understand the positioning of the absorbent article 110 in three dimensions. For example, in a preliminary step for application of an absorbent article 110, the absorbent article 110 is opened up and laid out flat so a wearer can be positioned on top of the open absorbent article 110. Similarly, fastener indicia 230 are visual indicia that allow the automated system to perceive the positioning of the fastening system of the absorbent article 110. This function is important to allow the robotic system to be able to manipulate the ears 122 and fasteners. In other words, the system needs to be able to see the fasteners and distinguish them from the rest of the absorbent article 110, and to determine whether the fasteners are open and spread out.

In still another aspect of the present disclosure, the manipulation-enablement feature 200 includes manipulation indicia 240 disposed on one or both of the body-facing and garment-facing surfaces of the absorbent article 110. Manipulation indicia 240 are visual indicia that indicate to an automated system where to engage the absorbent article 110 to be able to position the absorbent article 110 correctly and to make sure the absorbent article 110 is properly opened and flattened. For example, manipulation indicia 240 can be disposed at the top and the bottom of the absorbent article 110 to indicate points at which the automated system should grab or otherwise engage the absorbent article 110.

The alignment, fastener, and manipulation indicia 220, 230, 240 can be of any suitable design, shape, pattern, color, size, and density that allow the automated robotic system to perceive, differentiate, and identify the alignment, fastener, and manipulation indicia 220, 230, 240. In various aspects, the alignment, fastener, and manipulation indicia 220, 230, 240 can be anything that stands out from the diaper, is distinguishable by the robotic system, and is associable with specific elements of the absorbent article 110. For example, the alignment, fastener, and manipulation indicia 220, 230, 240 can be alphanumeric or geometric, can be filled or shaded, unfilled or unshaded, or partially filled or shaded, or can be complex or combined shapes. In examples illustrated in FIG. 2, the edge of a leg opening can be indicated by cruciform shapes, and the left side the front panel can be indicated by filled circles. The center of the absorbent article 110 can be indicated by a cross within a square, and the waist edges can be indicated by partially filled or shaded rectangles. In the latter indicia, the arrangement of filled and unfilled portions of the rectangles can provide additional information to the robotic system.

The alignment, fastener, and manipulation indicia 220, 230, 240 can be applied to the absorbent article 110 by any suitable method including ink jet or other forms of printing, or can be attached to the absorbent article 110 by any suitable means. The alignment, fastener, and manipulation indicia 220, 230, 240 can be applied using inks or adhesives that are visible in the visible spectrum and this visible to the human eye, or the alignment, fastener, and manipulation indicia 220, 230, 240 can be applied using inks or adhesives that are visible in the ultraviolet spectrum and thus invisible to the human eye. Any combination of inks and adhesives can be used to make some or all of the alignment, fastener, and manipulation indicia 220, 230, 240 visible or invisible to the human eye.

In other aspects, any combination of indicia and information can be a part of the graphic designs of the absorbent article 110, or can be included on the packaging of the absorbent article 110.

In any of these aspects, the manipulation-enablement feature 200 is configured to assist the post-retail manipulation of the absorbent article 110 by the robotic device by providing help to align the robotic device with the absorbent article 110, by providing part of a mechanical interface between the robotic device and the absorbent article 110, or by providing both.

In an aspect of the present disclosure, the automated system can also include an absorbent article changing station. The changing station includes an application section including an application surface where the absorbent article 110 can be disposed in an unfastened and unused state. The changing station can also include a removal section including a removal surface configured for the removal of the absorbent article 110 from the wearer.

The automated system can include a record keeping function that automatically records changing data to insure a standard of care is met. Examples of the data that can be recorded include change time, duration of time in a wet absorbent article 110, the time it took to change the wearer, cleaning products/regimen, what absorbent article 110 was applied, how many are left in inventory, and skin condition.

In a first particular aspect, a system for removing and donning a disposable absorbent article by using a separate robotic device includes an absorbent assembly including longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly. The absorbent assembly also includes a pair of ears extending transversely outward from the opposite sides of the absorbent assembly in the back waist region, where each of the ears includes a body-facing surface with a primary first fastening-component that is selectively engageable with a primary second fastening-component in the front waist region of the absorbent assembly in a wear configuration of the article, and a garment-facing surface opposite the body-facing surface. The absorbent article also includes a manipulation-enablement feature configured to assist the post-retail manipulation of the absorbent article by the robotic device.

A second particular aspect includes aspect 1, wherein the manipulation-enablement feature includes an engagement member disposed on the garment-facing surface of each of the pair of ears, each engagement member configured to selectively engage the robotic device.

A third particular aspect includes one or more of aspects 1 and 2, wherein the engagement member is selected from hook material, loop material, a snap, an adhesive, and a cohesive.

A fourth particular aspect includes one or more of aspects 1-3, wherein the manipulation-enablement feature includes alignment indicia and fastener indicia disposed on one of the body-facing and garment-facing surfaces of the absorbent assembly.

A fifth particular aspect includes one or more of aspects 1-4, wherein the alignment indicia and the fastener indicia are visible in the visible light spectrum.

A sixth particular aspect includes one or more of aspects 1-5, wherein the alignment indicia and the fastener indicia are visible under ultraviolet light and invisible in the visible light spectrum.

A seventh particular aspect includes one or more of aspects 1-6, wherein the manipulation-enablement feature includes manipulation indicia disposed on one of the body-facing and garment-facing surfaces of the absorbent assembly.

An eighth particular aspect includes one or more of aspects 1-7, wherein the manipulation indicia are visible in the visible light spectrum.

A ninth particular aspect includes one or more of aspects 1-8, wherein the manipulation indicia are visible under ultraviolet light and invisible in the visible light spectrum.

A tenth particular aspect includes one or more of aspects 1-9, wherein the manipulation-enablement feature is configured to assist the post-retail manipulation of the absorbent article by the robotic device by aligning the robotic device with the absorbent article.

An eleventh particular aspect includes one or more of aspects 1-10, wherein the manipulation-enablement feature is configured to assist the post-retail manipulation of the absorbent article by the robotic device by providing part of a mechanical interface between the robotic device and the absorbent article.

A twelfth particular aspect includes one or more of aspects 1-11, further including a changing station including an application section, the application section including an application surface wherein the absorbent assembly can be selectively disposed in an unfastened and unused state; and a removal section including a removal surface configured for the removal of the absorbent assembly from the wearer.

In a thirteenth particular aspect, a system for removing and donning a disposable absorbent article by using a separate robotic device includes an absorbent assembly including longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly. The absorbent article also includes a pair of ears extending transversely outward from the opposite sides of the absorbent assembly in the back waist region, each of the ears including a body-facing surface with a primary first fastening-component that is selectively engageable with a primary second fastening-component in the front waist region of the absorbent assembly in a wear configuration of the article, and a garment-facing surface opposite the body-facing surface. The system also includes a manipulation-enablement feature configured to assist the post-retail manipulation of the absorbent article by the robotic device, wherein the manipulation-enablement feature includes at least one of an engagement member disposed on the garment-facing surface of each of the pair of ears, each engagement member configured to selectively engage the robotic device, alignment fastener indicia disposed on one of the body-facing and garment-facing surfaces of the absorbent assembly, and manipulation indicia disposed on one of the body-facing and garment-facing surfaces of the absorbent assembly.

A fourteenth particular aspect includes aspect 13, wherein the engagement member is selected from hook material, loop material, a snap, an adhesive, and a cohesive.

A fifteenth particular aspect includes one or more of aspects 13-14, wherein the alignment indicia, the fastener indicia, and the manipulation indicia are visible in the visible light spectrum.

A sixteenth particular aspect includes one or more of aspects 13-15, wherein the alignment indicia, the fastener indicia, and the manipulation indicia are visible under ultraviolet light and invisible in the visible light spectrum.

In a seventeenth particular aspect, a method for removing and donning a disposable absorbent article using a separate robotic device includes providing a system including an absorbent assembly including longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly. The absorbent article also includes a pair of ears extending transversely outward from the opposite sides of the absorbent assembly in the back waist region, each of the ears including a body-facing surface with a primary first fastening-component that is selectively engageable with a primary second fastening-component in the front waist region of the absorbent assembly in a wear configuration of the article, and a garment-facing surface opposite the body-facing surface. The absorbent article also includes a manipulation-enablement feature configured to assist the post-retail manipulation of the absorbent article by the robotic device. The method also includes providing a changing station including an application section, the application section including an application surface wherein the absorbent assembly can be selectively disposed in an unfastened and unused state; and a removal section including a removal surface configured for the removal of the absorbent assembly from the wearer. The method also includes engaging the separate robotic device for the placement of an unused, unfastened absorbent assembly onto the application surface such that the garment-facing surface is directly or indirectly adjacent to the application surface.

An eighteenth particular aspect includes aspect 17, wherein the manipulation-enablement feature includes an engagement member disposed on the garment-facing surface of each of the pair of ears, each engagement member configured to selectively engage the robotic device.

A nineteenth particular aspect includes one or more of aspects 17 and 18, wherein the manipulation-enablement feature includes alignment indicia and fastener indicia disposed on one of the body-facing and garment-facing surfaces of the absorbent assembly.

A twentieth particular aspect includes one or more of aspects 17-19, wherein the manipulation-enablement feature includes manipulation indicia disposed on one of the body-facing and garment-facing surfaces of the absorbent assembly.

When introducing elements of the present disclosure or the preferred aspect(s) thereof, the articles "a", "an", "the", and "said" are intended to mean that there are one or more of the elements. The terms "comprising," "including", and "having" are intended to be inclusive and mean that there can be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed:

1. A system for removing and donning a disposable absorbent article by using a separate robotic device, the system comprising:
   an absorbent assembly comprising longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly;
   a pair of ears extending transversely outward from the opposite sides of the absorbent assembly in the back waist region, each of the ears comprising
      a body-facing surface with a primary first fastening-component that is selectively engageable with a primary second fastening-component in the front waist region of the absorbent assembly in a wear configuration of the article, and
      a garment-facing surface opposite the body-facing surface; and
   a manipulation-enablement feature configured to assist the post-retail manipulation of the absorbent article by the robotic device, wherein the manipulation-enablement feature comprises:
      an engagement member disposed on the garment-facing surface of each of the pair of ears, each engagement member configured to selectively engage the robotic device;
      fastener indicia disposed on at least one of the body-facing and the garment-facing surfaces of the absorbent assembly, the fastener indicia indicating to the separate robotic device to perceive the positioning of at least one of the primary first fastening-component and the primary second fastening-component; and
      manipulation indicia disposed on at least one of the body-facing and garment-facing surfaces of the absorbent assembly, the manipulation indicia indicating to the separate robotic device where to engage the disposable absorbent article to be able to position the disposable absorbent article and to open and flatten the disposable absorbent article.

2. The absorbent article of claim 1, wherein the engagement member is selected from hook material, loop material, a snap, an adhesive, and a cohesive.

3. The absorbent article of claim 1, wherein the manipulation-enablement feature further comprises alignment indicia disposed on at least one of the body-facing and garment-facing surfaces of the absorbent assembly, the alignment indicia indicating to the separate robotic device the positioning of the disposable absorbent article in three dimensions.

4. The absorbent article of claim 3, wherein the alignment indicia and the fastener indicia are visible in the visible light spectrum.

5. The absorbent article of claim 3, wherein the alignment indicia and the fastener indicia are visible under ultraviolet light and invisible in the visible light spectrum.

6. The absorbent article of claim 1, wherein the manipulation indicia are visible in the visible light spectrum.

7. The absorbent article of claim 1, wherein the manipulation indicia are visible under ultraviolet light and invisible in the visible light spectrum.

8. The absorbent article of claim 1, wherein the manipulation-enablement feature is configured to assist the post-retail manipulation of the absorbent article by the robotic device by aligning the robotic device with the absorbent article.

9. The absorbent article of claim 1, wherein the manipulation-enablement feature is configured to assist the post-retail manipulation of the absorbent article by the robotic device by providing part of a mechanical interface between the robotic device and the absorbent article.

10. The absorbent article of claim 1, further comprising a changing station comprising an application section, the application section comprising an application surface wherein the absorbent assembly can be selectively disposed in an unfastened and unused state; and a removal section comprising a removal surface configured for the removal of the absorbent assembly from the wearer.

11. A system for removing and donning a disposable absorbent article by using a separate robotic device, the system comprising:
   an absorbent assembly comprising longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly;
   a pair of ears extending transversely outward from the opposite sides of the absorbent assembly in the back waist region, each of the ears comprising
      a body-facing surface with a primary first fastening-component that is selectively engageable with a primary second fastening-component in the front waist region of the absorbent assembly in a wear configuration of the article, and
      a garment-facing surface opposite the body-facing surface; and
   a manipulation-enablement feature configured to assist the post-retail manipulation of the absorbent article by the robotic device, wherein the manipulation-enablement feature includes an engagement member disposed on the garment-facing surface of each of the pair of ears, each engagement member configured to selectively engage the robotic device, alignment indicia disposed on at least one of the body-facing and garment facing surfaces of the absorbent assembly, fastener indicia disposed on at least one of the body-facing and garment-facing surfaces of the absorbent assembly, and manipulation indicia disposed on at least one of the body-facing and garment-facing surfaces of the absorbent assembly, the manipulation indicia indicating to the separate robotic device where to engage the disposable absorbent article to be able to position the disposable absorbent article and to open and flatten the disposable absorbent article.

12. The absorbent article of claim 11, wherein the engagement member is selected from hook material, loop material, a snap, an adhesive, and a cohesive.

13. The absorbent article of claim 11, wherein the alignment indicia, the fastener indicia, and the manipulation indicia are visible in the visible light spectrum.

14. The absorbent article of claim 11, wherein the alignment indicia, the fastener indicia, and the manipulation indicia are visible under ultraviolet light and invisible in the visible light spectrum.

15. A method for removing and donning a disposable absorbent article using a separate robotic device, the method comprising:
providing a system comprising
an absorbent assembly comprising longitudinally opposite ends, transversely opposite sides, a front waist region, a back waist region, and a crotch region extending longitudinally between and interconnecting the front and back waist regions, a liquid permeable inner layer for facing a wearer that partly defines a body-facing surface, an outer layer for facing away from the wearer that defines a garment-facing surface, an absorbent body disposed between the inner and outer layers, at least one of the inner layer and outer layer defining the longitudinally opposite ends and transversely opposite sides of the absorbent assembly, the absorbent body having a pair of longitudinally extending sides and a pair of transversely extending ends, each of the longitudinally extending sides of the absorbent body being spaced inward from a respective one of the transversely opposite sides of the absorbent assembly,
a pair of ears extending transversely outward from the opposite sides of the absorbent assembly in the back waist region, each of the ears comprising
a body-facing surface with a primary first fastening-component that is selectively engageable with a primary second fastening-component in the front waist region of the absorbent assembly in a wear configuration of the article, and
a garment-facing surface opposite the body-facing surface; and
a manipulation-enablement feature configured to assist the post-retail manipulation of the absorbent article by the robotic device, wherein the manipulation-enablement feature includes manipulation indicia disposed on at least one of the body-facing and garment-facing surfaces of the absorbent assembly, the manipulation indicia indicating to the separate robotic device where to engage the disposable absorbent article to be able to position the disposable absorbent article and to open and flatten the disposable absorbent article;
providing a changing station comprising an application section, the application section comprising an application surface wherein the absorbent assembly can be selectively disposed in an unfastened and unused state; and a removal section comprising a removal surface configured for the removal of the absorbent assembly from the wearer; and
engaging the separate robotic device with the manipulation indicia for the placement of an unused, unfastened absorbent assembly onto the application surface such that the garment-facing surface is directly or indirectly adjacent to the application surface.

16. The method of claim 15, wherein the manipulation-enablement feature includes an engagement member disposed on the garment-facing surface of each of the pair of ears, each engagement member configured to selectively engage the separate robotic device.

17. The method of claim 15, wherein the manipulation-enablement feature includes alignment indicia and fastener indicia disposed on at least one of the body-facing and garment-facing surfaces of the absorbent assembly.

* * * * *